(12) United States Patent
Colin et al.

(10) Patent No.: US 6,458,553 B1
(45) Date of Patent: Oct. 1, 2002

(54) CARD FOR COUNTING AND CHARACTERIZING MICROORGANISMS

(75) Inventors: Bruno Colin, Marcy l'Etoile (FR); Cecile Paris, Marcy l'Etoile (FR); Thierry Sofia, Lyons (FR); Claude Terrot, Lyons (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/763,757

(22) PCT Filed: Sep. 1, 1999

(86) PCT No.: PCT/FR99/02082

§ 371 (c)(1), (2), (4) Date: May 14, 2001

(87) PCT Pub. No.: WO00/12674

PCT Pub. Date: Mar. 9, 2000

(30) Foreign Application Priority Data

Sep. 1, 1998 (FR) .............................. 98 11053

(51) Int. Cl.$^7$ .............................. C12Q 1/02; C12Q 1/00
(52) U.S. Cl. ........................ 435/29; 435/4; 435/286.1; 435/286.5; 435/283.1
(58) Field of Search .......................... 435/29, 4, 286.1, 435/286.5, 283.1

(56) References Cited

U.S. PATENT DOCUMENTS

| | | |
|---|---|---|
| 4,018,652 A | 4/1977 | Lanham et al. .......... 195/103.5 |
| 4,077,845 A | 3/1978 | Johnson ................... 195/103.5 |
| 4,318,994 A | 3/1982 | Meyer et al. ............... 435/301 |
| 5,149,505 A | 9/1992 | English et al. ................ 422/99 |
| 5,518,892 A | 5/1996 | Naqui et al. .................. 435/29 |
| 5,700,655 A | 12/1997 | Croteau et al. ............... 435/30 |

FOREIGN PATENT DOCUMENTS

| | | |
|---|---|---|
| DE | 295 00 587 U1 | 5/1996 |
| EP | 0 282 840 A2 | 9/1988 |
| EP | 0 550 090 A1 | 7/1993 |
| EP | 0 745 856 A2 | 12/1996 |
| FR | 1 598 197 A | 7/1970 |
| WO | 200012674 A1 * | 3/2000 |

* cited by examiner

*Primary Examiner*—Louise N. Leary
(74) *Attorney, Agent, or Firm*—Oliff & Berridge, PLC (57) ABSTRACT

The invention concerns an analysis card as well as a method for filing such a card and the use of said card. Said card comprises a body consisting of: a zone for injecting into the card a biological fluid to be analyzed; a main duct supplying the biological fluid coming from the injection zone; at least two secondary ducts located in the extension of the main duct; and at least one well corresponding to each secondary duct. The invention is characterized in that each well constitutes a means for dispensing a specific volume of said biological fluid into at least two terminal analysis ducts, via a terminal duct for each analysis cavity and the volume to be analyzed is less than the total volume of all the analysis ducts. Although this concerns a particular embodiment wherein a biological fluid is transferred in parallel, in another embodiment the transfer may be carried out in series. The invention is particularly applicable in microbiology.

19 Claims, 5 Drawing Sheets

Section A-A

Fig. 6

Section B-B

CARD FOR COUNTING AND CHARACTERIZING MICROORGANISMS

The invention relates to an analysis card making it possible to count and characterize microorganisms or any other biological material, such as a nucleic acid or antibody, in a biological sample. The invention also relates to a method of filling such a card as well as to the use of this card.

The terms [sic] "biological sample" should be understood to mean a liquid sample resulting from the physical treatment, for example homogenization, or dissolution in a solvent, or from the biological treatment, such as enzymatic digestion, of solid or liquid products, possibly consisting of food products, of water, of blood.

Apart from the conventional counting method in Petri dishes, nonautomated methods are found in the prior art for quantifying microorganisms; these methods are mainly based on determining the Most probable number (MPN).

U.S. Pat. No. 5,700,655 describes an apparatus for quantification of biological material in a liquid sample. This apparatus consists of a plastic sheet obtained by thermoforming, the sheet itself consisting of analysis cavities of the same size and of a cover making it possible to maintain sterility. The method consists in firstly depositing the sample to be analyzed in the center of the sheet and then the reaction mixture supplied with the apparatus. The apparatus thus prepared is agitated so as to fill all the cavities in the identical manner and then the excess reaction mixture is eliminated. Finally, the sheet is incubated for a time long enough to reveal the presence of microbes in one or more wells.

However, this apparatus, like the conventional Petri dishes, only allows the sample to be diluted once. Knowing that the sample has to be diluted several times in order to be sure of being able to determine the concentration of germs contained in said sample, it will be necessary to repeat this operation at least once.

In addition, this apparatus has another major drawback. This drawback consists of the need to eliminate the surplus reaction mixture. Since this operation is carried out by tilting the sheet, certain cavities may lose a part of their content. The amount of liquid in the cavities will therefore no longer be identical, and consequently the determination of the amount of germs will be false.

Furthermore, eliminating the surplus reaction mixture results in the production of potentially contaminated waste, which has to be reprocessed. Likewise, this elimination of the surplus contaminates the outside of the apparatus, which then becomes a source of biological contamination for the operator and all other surfaces which come into contact with him.

Finally [sic], since the cavities are arranged concentrically, the read-out also takes place concentrically, which may be a source of error, especially as the positive cavities are often dispersed over the sheet.

Finally, the abovementioned apparatus still has the basic drawback of Petri dishes, namely the fact that it must absolutely be handled with care and horizontally while the medium is gelling, if this gelling function is provided, so as to prevent a sample from leaking or passing from one cavity to another, which results in handling artifacts.

U.S. Pat. No. 5,518,892 discloses another apparatus for quantification of microorganisms in a liquid medium. It comprises a bag, made in a material and obtained by thermoforming, which has an opening on one of its sides. The method consists in forming, by heating, impermeable compartments or cavities on the lower face of the bag, allowing various amounts of the sample to be separated. Once the wells have been formed, the reaction mixture is prepared by adding the sample to be analyzed to the reaction mixture supplied with the apparatus. The reaction mixture is then poured into the bag via the opening provided for this purpose. A check is made that all the cavities are properly filled and then, after heat sealing, the bag is incubated for a time long enough to reveal the presence of microorganisms in one or more cavities. The cavities may be of the same size or three series of different sizes. It is thus possible to use a single bag in order to simulate seeding according to several dilutions.

However, this system has certain drawbacks. Firstly, and unlike an automated and very precise industrial injection molding system, this apparatus cannot guarantee optimum molding quality making it possible to obtain cavities of perfectly identical capacity, since basically simple plastic sheets are used which are formed by thermoforming. This is particularly important when a molding is produced with series of cavities of various volumes, especially when these are small volumes. Secondly, the reaction mixture is introduced by hand and the distribution in the cavities therefore takes place randomly. Thus, there may be no certainty that the volume of reaction mixture delivered into each cavity is the same, even if the size of the cavities is perfectly identical. The results may therefore again be false. Thirdly, the cavities are isolated by heat sealing at temperatures above 180° C., which carries the risk of irreversibly impairing (destroying the biological material to be analyzed and/or evaporating all or some of the liquid containing said material) the sample fraction contained in the cavities. This is all the more sensitive the smaller the size of the cavities and the smaller the amount of liquid they contain. This handling may therefore falsify the results of the counting and of the characterization.

According to the present invention, the analysis card proposed helps to overcome all of the abovementioned drawbacks.

This card makes it possible to fill all the cavities, whatever their size, which is proportional from one cavity to another, and which does not require positioning precautions to be taken when filling it. By "proportional from one cavity to another" is meant that when two cavities have the same dimensions, the proportion will then be substantially 1 for 1, or when two cavities have different dimensions, the proportion is different from 1 for 1. Moreover, there is no risk of contamination, on the one hand, of the specimen with the outside, since the liquid remains confined, and, on the other hand, between the various cavities of the card, since an isolating separation is also provided between each cavity of said card.

For this purpose, the present invention relates, according to a first preferred embodiment, to an analysis card which comprises a body consisting of:

a region for injecting a biological liquid to be analyzed into the card, a main feed channel for the biological liquid coming from the injection region, at least two secondary channels lying in the extension of the main channel, and at least one well corresponding to each secondary channel, characterized in that each well constitutes a means of delivering a predetermined volume of said biological liquid into at least two terminal analysis cavities, via a terminal channel for each analysis cavity, and in that the total volume to be analyzed is less than the total volume of all of the analysis cavities.

According to a second preferred embodiment of the invention, the analysis card which comprises a body consisting of:
a region for injecting a biological liquid to be analyzed into the card,
at least two feed channels for the biological liquid coming from the injection region, and
at least one well corresponding to each feed channel,
[lacuna] characterized in that each well constitutes a means of delivering a predetermined volume of said biological liquid into at least two terminal analysis cavities, via a terminal channel for each analysis cavity, and in that the volume to be analyzed is less than the total volume of all of the analysis cavities.

According to the above two embodiments, the delivery of the biological liquid into the terminal analysis cavities takes place in parallel.

According to a third preferred embodiment of the invention, the analysis card which comprises a body consisting of:
a region for injecting a biological liquid to be analyzed into the card,
a main feed channel for the biological liquid coming from the injection region,
at least two secondary channels lying in the extension of the main channel, and
at least one cavity corresponding to each secondary channel, characterized in that each cavity constitutes a means of receiving a predetermined volume of said biological liquid and in that the volume to be analyzed, introduced into the card, is greater than the total volume of all of the analysis cavities.

According to the previous embodiment, the delivery of the biological liquid into the analysis cavities takes place in series and is followed by a purge. According to the first embodiment, a well, acting as a main means of delivering the biological liquid, is present between, on the one hand, the main channel and, on the other hand, the secondary channels.

According to one of the two embodiments, the volumes of the secondary channels are all identical.

In a preferred version of one of these three embodiments, the terminal analysis cavities are of at least two different volumes.

Preferably, the terminal analysis cavities are of three different volumes.

The ratio existing between two cavities of different volumes is between 1/5 and 1/20, 1/50 and 1/200 or 1/500 and 1/2000 and especially 1/10, 1/100 or 1/1000.

The cavities of the same volume are arranged geometrically, for example aligned or concentric, in order to facilitate the manual and/or automatic optical read-out.

The present invention also relates to the method of filling an analysis card, as presented in the first two embodiments, characterized in that it consists in:
connecting the injection region of the card to a volume of the biological sample to be analyzed,
creating a vacuum within and/or in the vicinity of said card,
breaking the vacuum so as, on the one hand, to transfer the biological liquid into the analysis cavities and, on the other hand, to isolate with an inert fluid the various fractions of the sample which come from said biological liquid and which are present in each of said analysis cavities, and
analyzing the result obtained so as to determine the amount of microorganisms or of any other biological material, such as nucleic acids, antibodies, present in the initial biological sample.

The present invention also relates to the method of filling an analysis card as presented in the third embodiment, characterized in that it consists in:
connecting the injection region or the outlet of the card to a volume of a biological sample to be analyzed,
creating a vacuum or an overpressure within and/or in the vicinity of said card so as to transfer the biological liquid into the cavities,
stopping the vacuum or the overpressure,
purging the main channel in order to isolate with an inert fluid the various fractions of the sample which come from said biological liquid and which are present in each of said analysis cavities, and
analyzing the result obtained so as to determine the amount of microorganisms or of any other biological component, such as nucleic acids, antibodies, present in the initial biological sample.

According to the first two embodiments of the card, once the vacuum has been broken, the isolating fluid is in contact with the biological liquid either in the secondary channels or feed channels or in the analysis cavities.

Preferably, the volume of the biological liquid to be analyzed is less than the total volume of all of the analysis cavities.

According to the third embodiment of the card, the volume of the biological liquid to be analyzed is greater than or equal to the total volume of all of the analysis cavities, of all of the fluid circuit and of the overflow.

Preferably, the volume of the biological liquid to be analyzed is greater than or equal to the total volume of all of the analysis cavities and of all of the fluid circuit.

According to the first two embodiments of the card, the ratio of the volume of the biological sample to be analyzed to the total volume of all of the analysis cavities is, for example, from 1/10 to 9/10, especially from 4/10 to 6/10, and preferably 5/10 .

Finally, the present invention relates to the use of an analysis card, as described above, for counting microorganisms using the technique of the most probable number.

The figures appended hereto are given by way of indication and have no limiting character on the scope of the present invention. They constitute several particular embodiments of said invention.

Finally.

The present invention essentially relates to an analysis card 1 or 21 or 101 shown in the appended figures.

Figure 1:
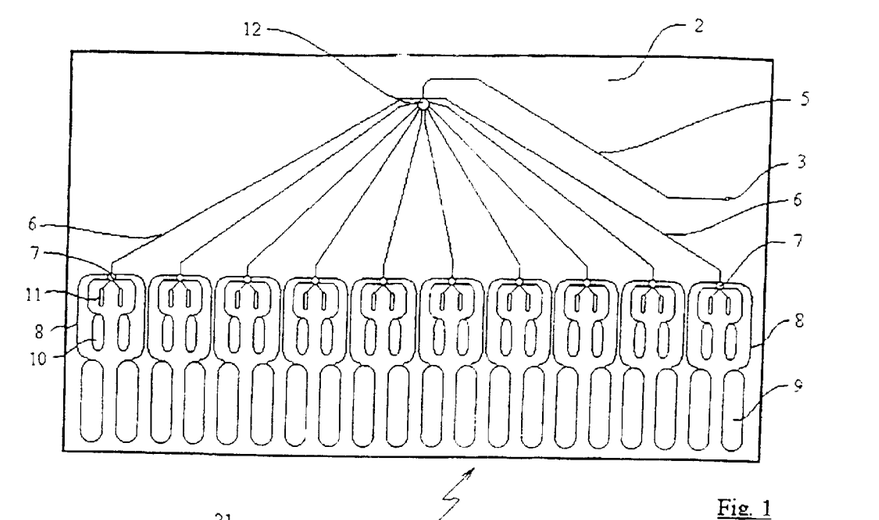
FIG. 1 shows a top view of a first embodiment of a card according to the invention, making it possible to count and characterize microorganisms in a biological sample.
Figure 2:
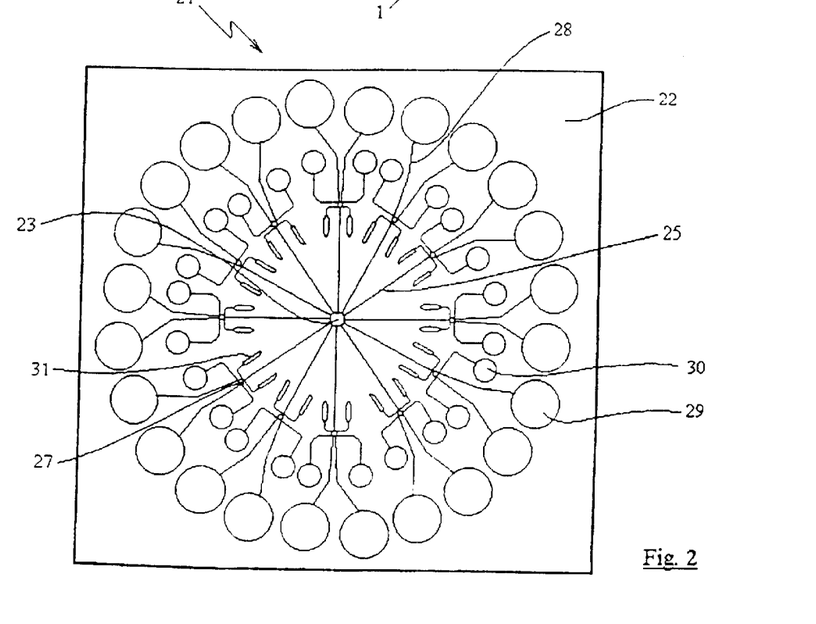
FIG. 2 shows a top view of a second embodiment of a card according to the invention, making it possible to count and characterize microorganisms in a biological sample.

Three particular embodiments are shown, namely a first embodiment of an analysis card 1 in FIGS. 1, 3, 4, 5 and 10, a second embodiment of an analysis card 21 in FIG. 2 and a third embodiment of an analysis card 101 in FIGS. 11 to 16.

Figure 3:
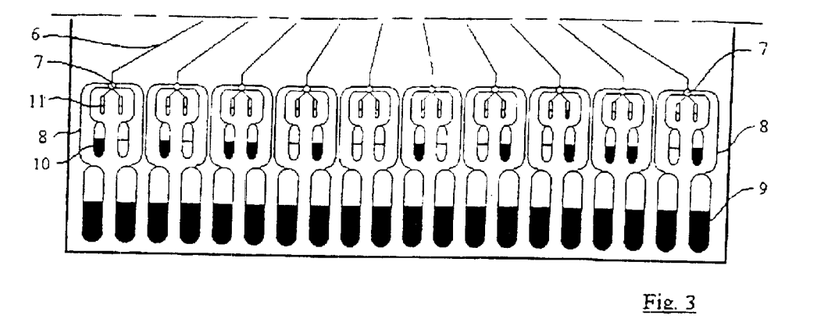
FIG. 3 shows an identical, but partial, view of FIG. 1, but in which the card has been used to count and characterize a population of microorganisms.

Referring now to FIGS. 1 and 3, the analysis card 1 essentially consists of a single monobloc element formed by the body 2 of the analysis card 1. This body 2 has a region 3 for injecting a biological sample 4 to be analyzed.

Figure 5:
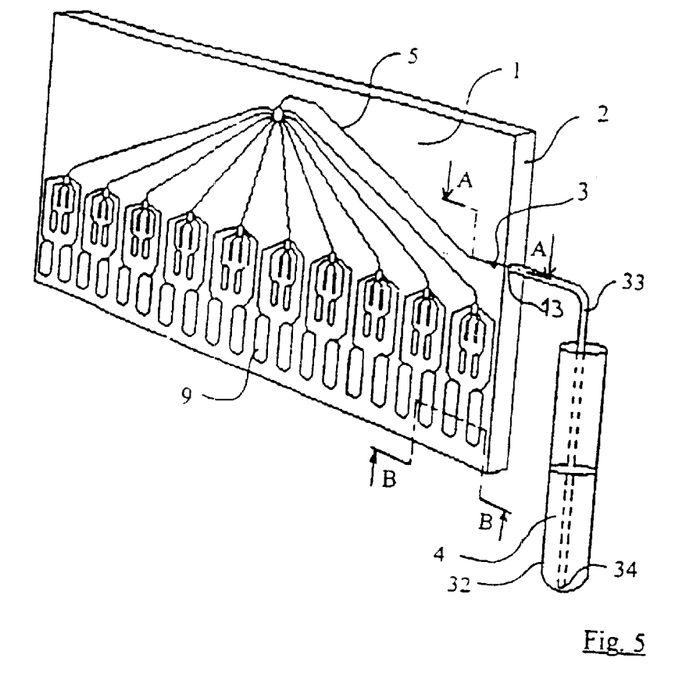
FIG. 5 shows a perspective view of an analysis card, as shown in FIGS. 1 and 3, which is linked via a tube to a container which contains the biological sample.

This injection region 3 may be on any face of the body 2, whether on the front face shown in FIG. 1 or 3, or on the rear face, or else on a side wall. This is, for example, the case in FIGS. 5 and 6, in which the injection region 13 is in a lateral position. In FIG. 5, the card 1 has not been filled with the sample 4 contained in the tube 32, but is connected to said sample via a flexible pipe 33. The assembly thus formed is ready to be positioned in a vacuum chamber.

Figure 6:
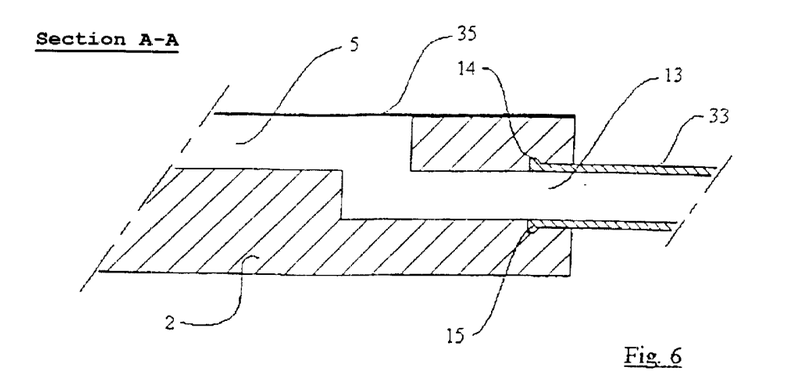
FIG. 6 shows a sectional view on A—A in FIG. 15.

FIG. 6 shows a section on A—A in FIG. 5. A main feed channel 5 forms a chicane so as to be directed toward the center of the body 2 of the card 1 and then extends within said card 1 toward one of its lateral surfaces so as to constitute the injection region 3. The link existing between the body 2 of the card 1 and the pipe 33 is provided by a circular groove 14, located in the body 2, and by a shoulder 15 of the pipe 33 fitting into the groove 14.

Of course, to do this, the body 2 has a substantially parallelepipedal shape. This body 2 is therefore monobloc and has a certain number of grooves and cavities 9, 10 or 11 lying within it. These cavities may consist of through-holes, as is the case in FIG. 7, or by blind holes, as is the case in FIG. 8.

These grooves and these blind holes are isolated from the outside by applying a transparent adhesive film 35 which is bonded to the surface of said body 2.

With regard to the grooves, it should firstly be noted that there is the main feed channel 5, which lies downstream of the injection region 3. Downstream of this channel 5 is a well 12 which acts as a main means of delivering the biological liquid 4 to be analyzed. In fact, the main channel 5 lies between the injection region 3 and the well 12. Likewise, there are secondary channels 6 which link this well 12 to a set of wells 7, where each well 7 corresponds to a channel 6. These wells 7 act as delivery means. Present in each of these wells 7 is a certain number of terminal channels 8, each channel 8 linking a well 7 to a terminal analysis cavity 9, 10 or 11.

In fact there are three types of terminal analysis cavities in these figures, namely large-sized terminal analysis cavities 9, medium-sized terminal analysis cavities 10 and finally small-sized terminal analysis cavities 11.

It will therefore be clearly understood that the cavities located on the body 2 of the analysis card 1 are, on the one hand, the grooves which are formed by the main channel 5, the secondary channels 6 and the terminal channels 8 and, on the other hand, the blind holes which are formed by the injection region 3, the well 12, the wells 7 and the set of analysis cavities 9, 10 and 11.

The analysis cavities 9, 10 and 11 of different sizes make it possible to dispense with the need to carry out dilutions. Thus, depending on the amount of liquid present in this analysis cavity 9, 10 or 11, there will be a greater or smaller number of microorganisms. Depending on the culture medium to be added, it will therefore be possible to grow certain microorganisms which, depending on whether they are present or not in each cavity 9, 10 or 11, will make it possible for the optical density to be modified or for a fluorescence or color (chromogenic effect) to appear or disappear. This will make it possible to detect the presence or absence of microorganism(s) and also to count them. Examples will be given later.

According to one particular embodiment, the dimensions of this card 1 are as follows:

the length of the card 1 is 135 mm;
the width of said card 1 is 85.5 mm;
the thickness of the card 1 is 4 mm;
the width of all the channels, referenced 5, 6 and 8, is 0.5 mm;
the depth of the main channel 5 is 0.5 mm;
the depth of the terminal channels 6 varies according to the distance of each channel 6 from a virtual axis passing through the well 12; this depth is:
 0.5 mm in the case of the outer channels 6,
 0.58 mm in the case of the central and outer channels 6,
 0.68 mm in the case of the central channels 6,
 0.79 mm in the case of the central and inner channels 6,
 0.87 mm in the case of the inner channels 6;
the depth of the terminal channels 8 is 0.5 mm;
the diameter and the depth of the main delivery means 12 are 3 mm and 1 mm, respectively;
the diameter and the depth of the delivery means 7 are 2 mm and 1 mm, respectively;
the position of the injection region 3 is located at 47.5 mm from the base of the card 1 and 5 mm into said card 1; it should be noted that this region 3 may be linked via a channel, not shown in this FIG. 1 to the field [sic] of the card 1, the diameter of which would be 2 mm;
the depth of the cavities 9 is 3.56 mm in the case of a 500 pressure card and is 2.34 mm in the case of a 250 pressure card, the length and the width of these cavities 9 being constant and 15 mm and 4.5 mm, respectively;
the depth of the cavities 10 is 2 mm in the case of a 500 pressure card and is 1.27 mm in the case of a 250 pressure card, the length and the width of these cavities 10 being constant and 6.5 mm and 2 mm, respectively, and
the depth of the cavities 11 is 0.88 mm in the case of a 500 pressure card and 0.53 mm in the case of a 250 pressure card, the length and the width of these cavities 11 being constant and 4 mm and 0.8 mm, respectively.

By "500 pressure card" is meant an analysis card 1 subjected to a vacuum of 500 mbar, i.e. 500 mbar of absolute pressure with respect to absolute vacuum. In the case of a "250 pressure card", the analysis card 1 is subjected to a vacuum of 750 mbar, i.e. 250 mbar of absolute pressure with respect to absolute vacuum. This is also true for the card 21, defined hereinbelow.

All the channels 5, 6 and 8 are produced by a ball-shaped milling cutter, whereas the cavities 9, 10 and 11 and the wells 3, 7 and 12 are produced by a cylindrical milling cutter. This is also true for the other cards 21 and 101.

According to a second embodiment shown in FIG. 2, the analysis card 21 is simpler since it is shown in starred form with an injection region 23 located at the center of the monobloc body 22 of the analysis card 21. In fact, this injection region 23 corresponds to the well 12 in FIG. 1, since it is from this region 23 that a certain number of feed channels 25 depart, these feed channels distributing the biological liquid 4 to be analyzed, not shown in this FIG. 2, around the periphery of the analysis card 21.

Each feed channel 25 links the injection region 23 to a well 27 acting as delivery means. Present after this well 27 are several terminal channels 28, each terminal channel 28 linking a well 27 directly to a terminal analysis cavity 29, 30 or 31 which has, similarly to the embodiment in FIG. 1, three different sizes ranging from the large size labeled 29 to the small size labeled 31, passing through the medium size labeled 30.

According to a particular embodiment, the dimensions of this card 21 are as follows:
the side of the card 21 is 135 mm;
the thickness of said card 1 is 4 mm;
the width and the depth of all the channels, labeled 25 and 28, are identical and equal to 0.5 mm;
the injection region 23 is a hole which may be a through-hole 2 mm in diameter;
the diameter and the depth of the delivery means 27 are 1.5 mm and 1 mm, respectively;
the depth of the cavities 29 is 2.85 mm in the case of a 500 pressure card and 1.88 mm in the case of a 250 pressure card, the diameter of these cavities 29 being 10 mm;
the depth of the cavities 30 is 1.88 mm in the case of a 500 pressure card and is 1.20 mm in the case of a 250 pressure card, the diameter of these cavities 30 being 4 mm; and
the depth of the cavities 31 is 0.85 mm in the case of a 500 pressure card and is 0.49 mm in the case of a 250 pressure card, the length and the width of these cavities 31 being 4 mm and 0.8 mm, respectively.

In this FIG. 2, the analysis cavities 29, 30 and 31 lie on a circular arc, which facilitates the read-out by an automatic system. Thus, the card 21 is rotated so that the cavities 29, 30 or 31 take it in turn to face the read head, not shown in the figures.

In contrast, in FIGS. 1 and 3 the read-out is linear because of the alignment of the various analysis cavities 9, 10 and 11. In addition, there is a separation between the large cavities 9, the medium cavities 10 and the small cavities 11, which are superposed one on top of another. This facilitates the visual read-out, while remaining suitable for an automatic read system.

Figure 7:
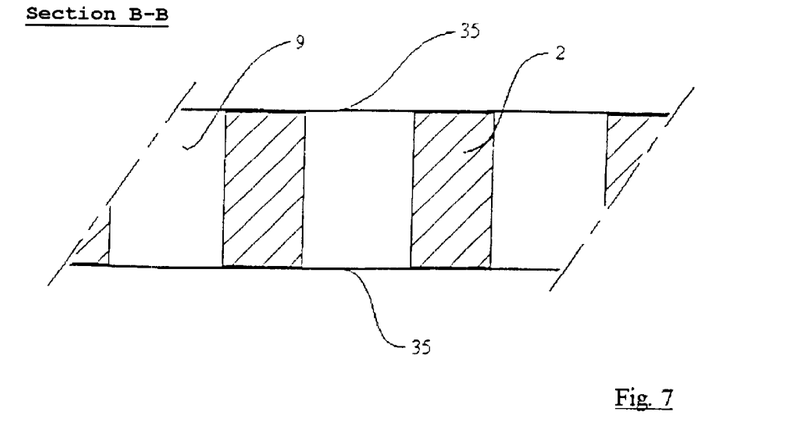
FIG. 7 shows a sectional view on B—B in FIG. 5.
Figure 8:
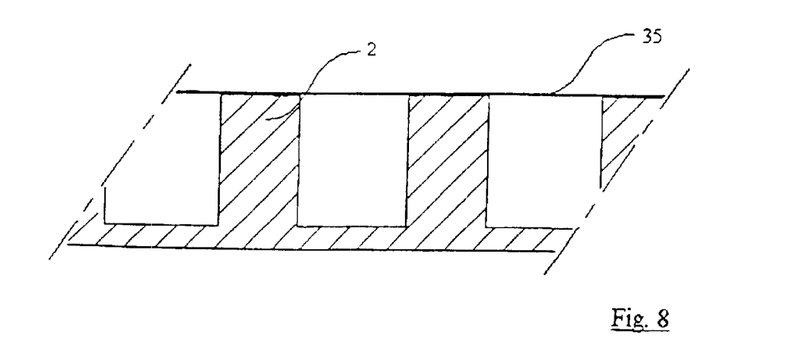
FIG. 8 shows a sectional view identical to that in FIG. 7, but in which the analysis card consists of another embodiment which is different in the cavities.

According to FIGS. 7 and 8, the cavities 9, 10 and 11 may be of different shapes. Thus, according to FIG. 7, the cavity is a through-cavity, that is to say the partitioning of each cavity requires the presence of two transparent adhesive films 35. It is also possible to have a single film 35 which sandwiches the card 1. This structure is particularly suitable for automated read-out of the optical density. In the case of FIG. 8, the cavity consists of a blind hole-only a single film 35 is used to partition the space in said cavity.

The transparent adhesive film 35 is of beneficial use since, after it has been cut or it has shrunk, it allows a user to have direct access to the contents of the cavities 9 to 11 (FIG. 1) and 29 to 31 (FIG. 2).

To simplify the embodiment in FIGS. 1 and 3, it would be quite possible to inject the biological sample 4 to be analyzed directly into the well 12 and thus it is not necessary to have the injection region 3 and the main feed channel 5.

Reference will now be made to FIG. 1, although what will be explained below also relates to he other embodiment, shown in FIG. 2.

In order for the volumes delivered into each analysis cavity 9, 10 or 11 to be identical or proportional for each cavity 9, 10 or 11 of identical or different volumes, the various secondary channels 6 all have an identical volume. Thus, as clearly shown in FIG. 1, the secondary channels 6 lying at the center of the analysis card 1 are shorter in length than those lying at the sides. It would therefore be appropriate to vary their width or their depth so that the volumes are constant between all the channels 6. Likewise, the length of the terminal channels 8 is identical for each analysis cavity 9, 10 or 11 of identical volume.

In fact, there also exists a proportionality between the small cavities 11 and the large cavities 9, and with the medium cavities 10. Thus, the ratio [sic] existing between two cavities of different volumes, in the figures shown, are 1 to 10 between the cavities 10 and 9 and the cavities 11 and 10 and 1 to 100 between the cavities 11 and 9. This proportionality may also be repeated in the terminal channels 8, these terminal channels 8 having different dimensions depending on whether they feed large-sized cavities 9, medium-sized cavities 10 or finally small-sized cavities 11.

With regard to the structure of the analysis cards 1 and 21, all the channels, whether they are main channels 5, feed channels 25, secondary channels 6 or terminal channels 8 or 28, do not cross one another so as to avoid any contamination of one amount of sample located in one analysis cavity with respect to an amount of sample located in another analysis cavity. To do this, the points of intersection of these various channels among themselves are always made via wells acting not only as delivery means but also as a buffer volume preventing any contamination after introduction of the sample 4. At these wells, the transfer of liquid 4 to be analyzed takes place in parallel in all the downstream channels.

The method of filling an analysis card 1 or 21 therefore consists in:
linking the injection region 3 or 23 of the card 1 or 21 to a volume of the biological sample 4 to be analyzed;
generating a vacuum within and/or in the vicinity of said card 1 or 21;
gradually breaking the vacuum so that, on the one hand, the biological liquid is transferred into the analysis cavities 9, 10 and/or 11 or else 29, 30 and/or 31 and, on the other hand, air isolates the various fractions of the sample which come from said biological sample 4 and are present in each of said analysis cavities 9, 10 or 11 or else 29, 30 or 31.

Figure 4:
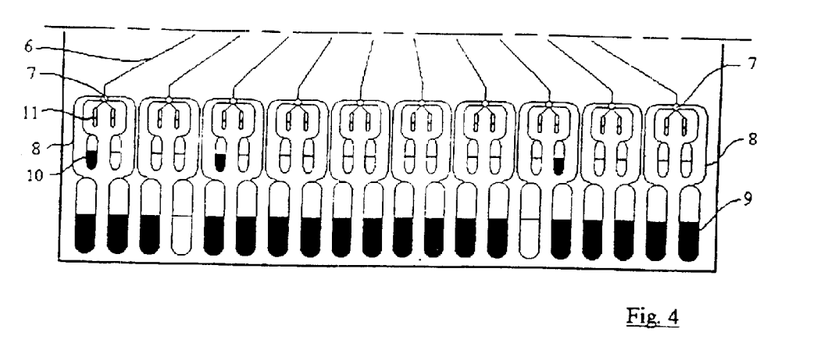
FIG. 4 shows an identical, but partial, view of FIG. 1, but in which the card has been used to count and characterize another population of microorganisms.

Consequently, once the vacuum has been broken, air comes into contact with the fractions of the biological sample 4, either in the terminal channels 8 according to FIGS. 1 and 3 or the terminal channels 28 according to FIGS. 2 and 4, or in the analysis cavities 9, 10 and 11 (FIG. 1) or else 29, 30 and 31 (FIG. 2). This creates a physical separation between the bacteria. Of course, this can only be achieved if the volume of the biological sample 4 is in a ratio with the total volume of the analysis cavities and, optionally, of the volume of the terminal channels 8 or 28.

Instead of air, it is possible to use any fluid, gaseous or liquid, which may provide this isolating function. Care must be taken to ensure that said fluid is substantially inert with respect to the biological compounds contained in the sample and is immiscible with said sample. If the fluid is a liquid, such as oil for example, it must have a lower density than the biological sample.

In this case, the card 1 must be maintained substantially in a vertical position, as shown in FIG. 5, the isolating fluid, not shown in the figures, being in a position above the biological sample contained in each cavity.

However, it is possible to use other techniques for physically isolating or separating the cavities 9, 10 and 11 or 29, 30 and 31. Thus, it is possible to add a gelling agent, such as peptine, to the biological sample 4 and at the middle of the culture, allowing microbial growth. In this case and when the gelling agent has acted, it is no longer necessary to keep the card 1 in a substantially vertical position.

Finally, said cavities 9, 10 and 11 or 29, 30 and 31 may be isolated by obstructing the terminal channels 8. It is possible to use, for example, an adhesive as isolating fluid, or the terminal channels may be obstructed by physical compression.

In one particularly beneficial way of filling using the method according to the invention, the volume of the biological sample 4 to be analyzed is less than the total volume of all of the analysis cavities 9, 10 and 11 (FIG. 1) or else 29, 30 and 31 (FIG. 2). This ratio of the volume of biological liquid 4 to the total volume of all of the analysis cavities 9, 10 and 11 is preferably one to two.

Moreover, the filling of the cavities 9, 10 and 11 or 29, 30 and 31 takes place simultaneously, at a given filling time, and the ratio between the volume of liquid present in each small, medium or large size of cavity to the total volume of each size of cavity, small, medium or large respectively, is constant for all of the cavities 9, 10 and 11 or 29, 30 and 31 of the card 1 or 21.

The third embodiment is clearly shown in FIGS. 11 to 16. It is distinguished from the first two embodiments, on the one hand, by its structure and, on the other hand, by its operation. Thus, the particular structure of this embodiment allows transfer of the liquid 4 to be analyzed which is carried out in series and not in parallel, as was the case with the first two embodiments.

Figure 11:
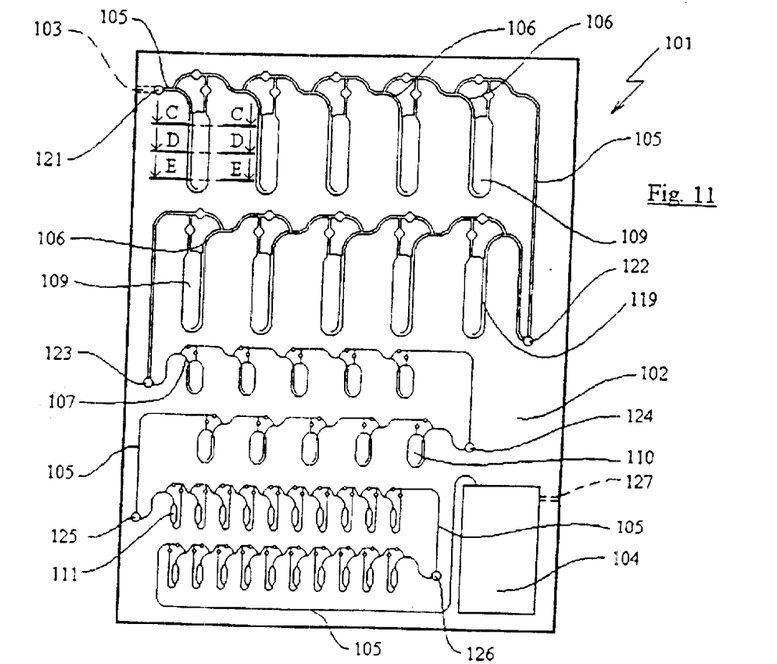
FIG. 11 shows a top view of a third embodiment of a card according to the invention, making it possible to count and characterize microorganisms in a biological sample.

FIG. 11 allows the operation associated with this structure to be clearly understood. The analysis card 101 comprises, in a similar manner to the previous cards 1 and 21, a body 102 provided laterally with an injection region 103. According to one particular embodiment, this region 103 lies in the extension of the main feed channel 105, which travels over the entire card 101 before terminating in a reservoir acting as an overflow 104, the overflow 104 itself being linked to the outside via an outlet 127. It should be noted that all of the analysis cavities 109, 110 and 111 are branched off from the main channel 105. Each of these branch-offs is labeled 115 at said cavities 109, 110 and 111, and the same applies even if they are an integral part of this main channel 105. The structure of the card 101 and of its constituents influences the liquid 4 in its movement so that the filling of the cavities 109, 110 and 111 is carried out, but by isolating the aliquots present in each of said cavities 109, 110 and 111. Such a structure and its operation have already formed the subject of studies by the Applicant, and this has resulted in the filing of a patent application FR 98/03033 filed on Mar. 9, 1999.

This card 101 again comprises ten large-sized terminal analysis cavities 109, ten medium-sized terminal analysis cavities 110 and ten small-sized terminal analysis cavities 111. For space reasons, each group of identically sized cavities 109, 110 or 111 is distributed over two rows, thereby facilitating the visual read-out of said card 101. The large-sized cavities 109 and the medium-sized cavities 110 have almost identical structure and essentially use gravity (in the cavities 109 and 110 ) associated either with a vacuum applied at the outlet 127 or an overpressure applied at the inlet 103 (in the main channel 105 ) in order to direct the sample 4, whereas the small-sized cavities 111 have a different structure and essentially use the capillary effect to fill them with said sample 4. The vacuum applied at the outlet 127 or the overpressure applied at the inlet 103 may be between more or less 5 to 20 mbar and preferably 10 mbar.

Referring to FIG. 11, the medium-sized cavities 110, and therefore also the large-sized cavities 109, have an intersection between the main channel 105 and the secondary channels 106, and therefore 107. Each secondary channel 106 and 107 terminates in the upper and lateral position of the cavity 109 or 110 in question. The upper and central end of said cavity 109 or 110 links it to the main feed channel 105, which channel 105 is directed toward the next cavity 109, 110 or 111 via an upper branch-off 113. Upstream of this main channel 105/ upper branch-off 113 link there are two wells 112 and 114. The main channel 105 has, in a branch-off 115 for bypassing each cavity 109 and 110, a well 112 which slows down the flow of the sample 4, the preferred direction being the direction of the secondary channel 106 or 107, by gravity. The upper branch-off 113 also has a well 114 which prevents flow of the sample 4, the preferred direction being the flow of the liquid 4 toward other cavities via the main channel 105, by suction.

Figures 12, 13, 14, 15, 16:
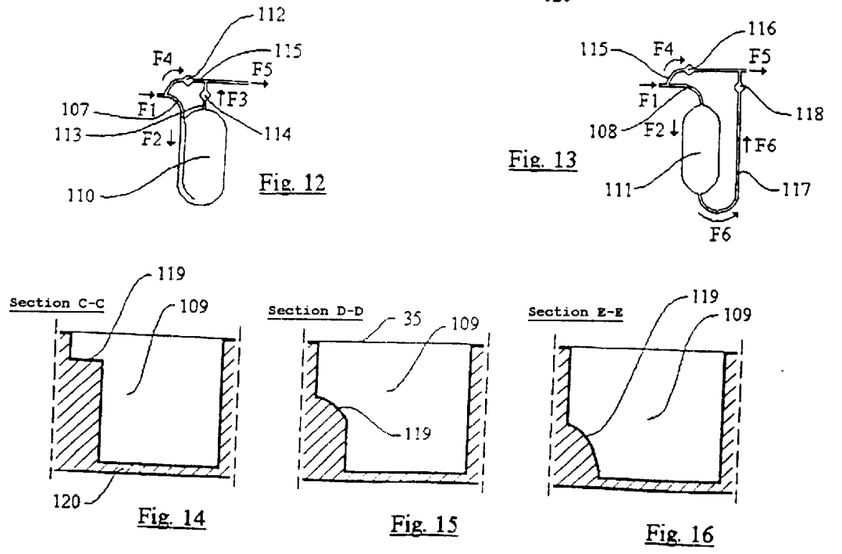
FIG. 12 shows a detailed view of an analysis cavity of moderate size.
FIG. 13 shows a detailed view of an analysis cavity of small size.
FIG. 14 shows a sectional view on C—C in FIG. 11.
FIG. 15 shows a sectional view on D—D in FIG. 11.
FIG. 16 shows a sectional view on E—E in FIG. 11.

Referring now to FIG. 13, the small-sized cavities 111 have an intersection between the main channel 105 and the secondary channels 108. Each secondary channel 108 terminates in the upper and central position of the cavity 111 in question. The lower and central end of said cavity 111 connects it to the main feed channel 105, which is directed toward the next cavity 111 or the outlet 127, by a lower branch-off 117. Upstream of this main channel 105/lower branch-off 117 link there are two wells 116 and 118. The well 116 is present upstream in the channel 105 and the well 118 is present upstream in the branch-off 117. The main channel 105 has, at each cavity 111, a well 116 which slows down the flow of the sample 4, the preferred direction being the direction of the secondary channel 108, by capillary effect. The lower branch-off 117 also has a well 118 which prevents the flow of the sample 4, the preferred direction being the flow of the liquid 4 toward other cavities, via the main channel 105, by suction.

The main channel 105 is labeled 115 at:
the cavities 109 between the main channel 105/secondary channel 106 link and the main channel 105 upper branch-off 113 link;
the cavities 110 between the main channel 105/secondary channel 107 link and the main channel 105/upper branch-off 113 link;
the cavities 111 between the main channel 105 secondary channel 108 link and the main channel 105/lower branch-off 117 link.

FIG. 11 also shows the presence of various retarding wells 121, 122, 123, 124, 125 and 126. These retarding wells 121, 122, 123, 124, 125 and 126 allow possible control of the movement of the liquid 4 to be analyzed, if it is desired to fill only all or some of the cavities 109 or 109 and 110 or 109, 110 and 111. Although this is not shown in FIG. 11, it is possible to have, in addition, two valves, fitted in the main channel 105, before the first cavity 109 and after the last cavity 111, so as to considerably reduce the risks of internal contamination of the card 101. One of the valves could be fitted at the retarding well 121 and the other before the overflow 104. Such valves have already been described in the two patent applications FR 98/11383 and FR 99/07689 filed by the Applicant and dated Sep. 8, 1998 and Jun. 14, 1999, respectively.

FIGS. 12 and 13 show in greater detail the movement of the fluids (liquid 4 and air) contained in the card 101.

According to FIG. 12, the liquid 4 arrives via the main channel 105 in the direction F1 and flows, preferably in the direction F2, into the cavity 110 via the secondary channel 106. The cavity 110 then fills until the liquid 4 comes into contact with the lower opening in the upper branch-off 113. At this point, only air is expelled in the direction F3 toward the main channel 105. The liquid 4 then takes the direction of the bypass branch-off 115 in the direction F4 so as to flow out in the direction F5 toward another cavity 110 or 111. The bypass branch-off 115 has a well 112 which creates a pressure drop at this point, thereby making the liquid choose the easier path, namely the secondary channel 107 and slowing down its flow at this point. The upper branch-off 113 has a well 114 which also creates a pressure drop at this point and prevents flow of said liquid 4, which forces the liquid to choose the easier path, namely the bypass branch-off 115.

According to FIG. 13, the liquid 4 arrives via the main channel 105 in the direction F1 and flows, preferably in the direction F2, into the cavity 111 via the secondary channel 108. The cavity 111 therefore fills completely and then the liquid 4 starts to flow in the direction F6 into a lower branch-off 117. Nevertheless, since the pressure drop is very great at this point, the liquid 4 then takes the direction of the bypass branch-off 115 in the direction F4 so as to flow out in the direction F5 toward another cavity 111 or the overflow 104 and thereafter the outlet 127. The pressure drop is larger if there is, in this branch-off 117, a well 118 which prevents said liquid 4 from returning to the main channel 105. At this point, the air is therefore also forced out in the direction F6 toward said main channel 105. The bypass branch-off 115 has a well 116 which creates a pressure drop at this point, thereby forcing the liquid 4 to choose the easier path, namely the secondary channel 108.

The total volume of liquid 4 transferred within the card 101 is greater than the total volume of all of the cavities 109, 110 and 111 and is less than or equal to the sum of the total volume of all of said cavities 109, 110 and 111, of all of the channels and branch-offs and of the volume of the overflow 104. In one embodiment, the level of the liquid 4 which is present in said overflow 104 and which flows out at this point under gravity is below the point of insertion of the outlet 127 on the overflow 104. The aim is to allow air, once the liquid 4 has filled all of the cavities 109, 110 and 111, to replace said liquid 4 in the main feed channel 105 so as to create an isolation between all of said cavities 109, 110 and 111.

Preferably, the total volume of liquid 4 transferred within the card 101 is less than or equal to the sum of the total volume of all of said cavities 109, 110 and 111. Consequently, it is possible to purge, with air or with any other inert fluid for the analyses that have to be carried out, the main channel 105 of any liquid 4 once all the cavities 109, 110 and 111 have been filled. This purge allows the contents of all the cavities to be isolated from one another.

As was mentioned earlier, the large-sized cavities 109 and the medium-sized cavities 110 operates [sic] by the liquid 4 flowing under gravity, whereas the small-sized cavities 111 operates [sic] by capillary effect. Moreover, the orders of magnitude which will be given below with regard to the internal and external dimensions of the card 101 will demonstrate these phenomena.

In FIGS. 14, 15 and 16 it should be noted that, in order to further facilitate transfer into the large-sized cavities 109 and medium-sized cavities 110, these cavities 109 and 110 are equipped with a draining means 119 of quite particular shape depending on the distance separating it from the inlet of said cavity 109 or 110, corresponding to the secondary channel 106 or 107. Thus, whereas the draining means 119 has the form of a shoulder as close as possible to this inlet, with an edge between this means 119 and the side wall of the cavity 109 or 110, this angle gradually disappears to be replaced by a curve which continues until joining the bottom 120 of the body 102 of said card 101.

The dimensions of this card 101 are given by way of nonlimiting example. Thus, the card 101 has a width of 108 mm, a length of 118 mm and a thickness of 4 mm. The other dimensions are as follows:

the main channel 105, and therefore the branch-offs 115, has a U-shaped cross section, the opening of which is closed by the film 35, and the width and the depth of this U are 0.5 mm;

the upper branch-offs 113 and the lower branch-offs 117 have a U-shaped cross section, the opening of which is closed by the film 35, and the width and the depth of this U are 0.2 mm;

the depth, the length and the width of the large-sized cavities 109 are 3.1 mm, 20 mm and 5.5 mm, respectively;

the depth, the length and the width of the medium-sized cavities 110 are 1.8 mm, 6 mm and 3.5 mm, respectively;

the depth, the length and the width of the small-sized cavities 111 are 1 mm, 3 and 1 mm, respectively;

the depth, the length and the width of the overflow 104 are 3.6 mm, 25 mm and 24 mm, respectively;

the diameter of the wells 112, at the cavities 109, is 2 mm—each well is a spherical cap 1 mm in depth, produced by a milling cutter in the form of a ball 2 mm in diameter;

the diameter of the wells 112, at the cavities 110, is 1.5 mm, as is the diameter of the wells 114 at the cavities 109 and 110 and of the wells 116 and 118 of the cavities 111—each well is a spherical cap 0.75 mm in depth, produced by a milling cutter in the form of a ball 1.5 mm in diameter;

the outlet channel 127 has a U-shaped cross section, the opening of which is closed by the film 35 and the width and the depth of this U are respectively 1 mm and 0.5 mm; and the retarding wells 122, 123, 124, 125 and 126 all have a diameter of 3 mm—each well is a spherical cap 1.5 mm in depth, produced by a milling cutter in the form of a ball 3 mm in diameter.

The procedure allowing the microorganisms contained in a biological sample 4 to be counted can be used in the food field. In the example given below, the procedure is as follows.

It firstly consists in preparing a liquid sample 4. Thus, for a weight of about 10 grams of a food product, 90 ml of peptone water are added to a Stomacher bag with filter. The sample in the Stomacher bag is homogenized for 1 to 2 minutes. A $10^{-1}$ first dilution is thus obtained. Further dilutions are made by transferring 1 ml of the liquid contained in said Stomacher bag to a flask containing 49 ml of a culture medium, and the mixture is then homogenized. The dilution is therefore $2 \times 10^{-3}$, i.e. 1/500.

Knowing that the volume of the large-sized cavities 9 is 200 μl, of the medium-sized cavities 10 is 20 μl and of the small-sized cavities 11 is 2 μl, given that there are twenty cavities 9, 10 or 11 of each size, the total volume of said cavities 9, 10 or 11 is 4440 μl. It should be noted that these numbers are given by way of example. It is quite possible, for example, to have a number of cavities 9, 10 and 11 which can vary from one size of cavity to another.

In order to comply with the pre-established ratio of the volume of biological liquid 4 to the total volume of all of the cavities of one to two, 2220 μl are therefore transferred from this flask into a tube 32. A flexible pipe 33 is either present at the card 1 and forms with the latter the consumable, or is linked to said card before its use. The tube 32 is placed vertically on a support and the content of the tube 32 is linked via the flexible pipe 33 to the injection region 3 of the card 1. The whole assembly thus formed, and shown in FIG. 5, is then placed in a vacuum so that the sample 4 contained in said tube 32 is ready to be transferred completely into the analysis cavities 9, 10 or 11. Next, the vacuum is gradually broken, that is to say in at least 10 seconds.

Figure 9:
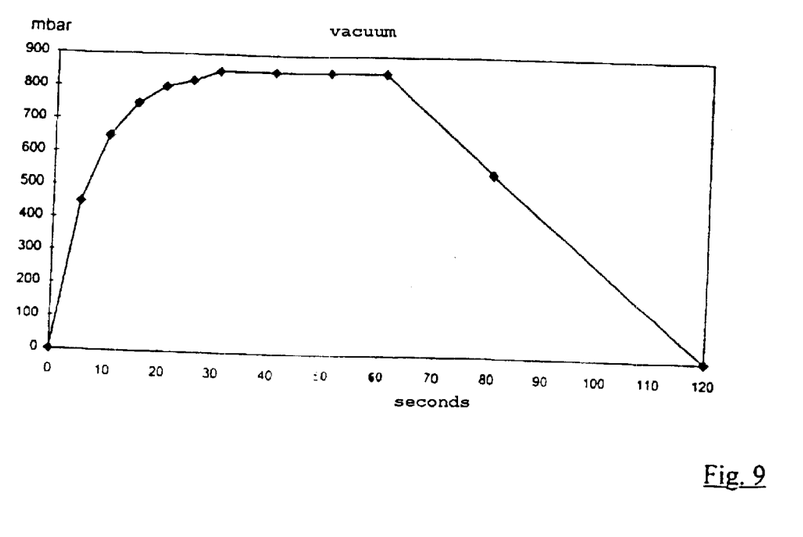
FIG. 9 illustrates a curve showing the variation in the pressure within a vacuum bell in which the assembly, formed by the card, the specimen, the tube and the pipe, is placed in a position making it possible thereafter to transfer said sample into the cavities of said card.

Thus, FIG. 9 clearly shows that the reduced pressure exerted in order to obtain a suitable vacuum, even a partial vacuum, must be approximately 850 millibars and is reached in one minute. Likewise, the return to normal pressure takes place gradually in one minute. Next, the entire apparatus is removed from the vacuum chamber. The analysis card 1 is hermetically sealed by cutting and sealing off at the pipe 33, at the point where it is flush with the lateral surface of said card 1, and then the tube 32 is removed. The card is left in the vertical position. The latter point is not an absolute necessity. In this position, the various cards 1 are incubated for about 24 hours at 30° C.

Thus, 100, 10 and 1 µl of the biological sample have been distributed in each of the cavities 9, 10 and 11, respectively.

Finally, it is possible to read the card 1 by counting the number of analysis cavities 9, 10 and/or 11 which have been modified in terms of their optical density or of their coloration, in the case of the use of a fluorescent or chromogenic marker. In all circumstances, this corresponds to development of the microorganism type that it is desired to reveal. According to the number of large-sized analysis cavities 9, medium-sized analysis cavities 10 and small-sized analysis cavities 11 which have changed appearance, it is possible to refer to table 1, which follows, in order to determine the precise amount of the microorganism within the initial sample.

The most probable number (NPP) of bacteria in a sample is calculated using a statistical method, explained by R. J. Parnow (1972); Cf. PARNOW R J, 1972—Computer program estimates bacterial densities by means of the most probable numbers, Food Technology 7, 56–62. However, this method gives all of the existing combinations for the three numbers of positive tubes, yet there are combinations which are highly improbable or statistically incorrect. For example, it is inconceivable to have no positive tube in the cavities containing 100 µl of sample (first dilution) and to have twenty thereof in the cavities containing 1 µl of sample (third dilution).

Thus, the probability of an appearance is associated with each combination of positives. To do this, the method of J. C. De Man (1975) is used; Cf. DE MAN J., 1975—The probability of most probable numbers, European Journal of Applied Microbiology, 1, 67–68; then, again according to this author, various combinations of positives are defined:

category 1 comprises all the highest-probability combinations, the sum of the probabilities of which is 95%;

category 2 comprises all the combinations, the sum of the probabilities of which represents the next 4%; and category 3 comprises all the combinations, the sum of the probabilities of which represents the remaining 1%.

In table 1 below, only the combinations of category 1 appear, with the MPNs which are associated therewith. Since the table takes no account of dilution, the MPN found in this table 1 must therefore be multiplied by the total dilution factor in order to obtain the level of contamination of the initial sample.

TABLE 1 table of the various combinations of positive cavities in order to determine the initial concentration in the sample by the Most Probable Number (MPN) technique.

| Number of positive cavities | | | | Number of positive cavities | | | | Number of positive cavities | | | |
|---|---|---|---|---|---|---|---|---|---|---|---|
| 100 µl | 10 µl | 1 µl | MPN | 100 µl | 10 µl | 1 µl | MPN | 100 µl | 10 µl | 1 µl | MPN |
| 0 | 1 | 0 | 0.45 | 11 | 3 | 0 | 8.89 | 16 | 4 | 1 | 17.9 |
| 1 | 0 | 0 | 0.46 | 11 | 4 | 0 | 9.60 | 16 | 5 | 0 | 18.0 |
| 1 | 1 | 0 | 0.92 | 12 | 0 | 0 | 7.78 | 16 | 5 | 1 | 19.1 |
| 2 | 0 | 0 | 0.94 | 12 | 1 | 0 | 8.49 | 16 | 6 | 0 | 19.2 |
| 2 | 1 | 0 | 1.42 | 12 | 1 | 1 | 9.19 | 17 | 0 | 0 | 14.5 |
| 2 | 2 | 0 | 1.90 | 12 | 2 | 0 | 9.22 | 17 | 1 | 0 | 15.6 |
| 3 | 0 | 0 | 1.45 | 12 | 2 | 1 | 9.92 | 17 | 1 | 1 | 16.7 |
| 3 | 1 | 0 | 1.94 | 12 | 3 | 0 | 9.95 | 17 | 2 | 0 | 16.8 |
| 3 | 2 | 0 | 2.43 | 12 | 4 | 0 | 10.7 | 17 | 2 | 1 | 17.9 |
| 4 | 0 | 0 | 1.99 | 13 | 0 | 0 | 8.81 | 17 | 3 | 0 | 18.0 |
| 4 | 1 | 0 | 2.49 | 13 | 1 | 0 | 9.57 | 17 | 3 | 1 | 19.1 |
| 4 | 2 | 0 | 3.00 | 13 | 1 | 1 | 10.3 | 17 | 4 | 0 | 19.2 |
| 5 | 0 | 0 | 2.55 | 13 | 2 | 0 | 10.4 | 17 | 4 | 1 | 20.4 |
| 5 | 1 | 0 | 3.07 | 13 | 2 | 1 | 11.1 | 17 | 5 | 0 | 20.5 |
| 5 | 2 | 0 | 3.60 | 13 | 3 | 0 | 11.1 | 17 | 5 | 1 | 21.8 |
| 6 | 0 | 0 | 3.15 | 13 | 3 | 1 | 11.9 | 17 | 6 | 0 | 21.9 |
| 6 | 0 | 1 | 3.68 | 13 | 4 | 0 | 11.9 | 17 | 6 | 1 | 23.2 |
| 6 | 1 | 0 | 3.69 | 13 | 5 | 0 | 12.8 | 17 | 7 | 0 | 23.3 |
| 6 | 2 | 0 | 4.24 | 14 | 0 | 0 | 9.96 | 18 | 1 | 0 | 17.9 |
| 6 | 3 | 0 | 4.78 | 14 | 1 | 0 | 10.8 | 18 | 2 | 0 | 19.3 |
| 7 | 0 | 0 | 3.79 | 14 | 1 | 1 | 11.6 | 18 | 2 | 1 | 20.6 |
| 7 | 1 | 0 | 4.35 | 14 | 2 | 0 | 11.6 | 18 | 3 | 0 | 20.7 |
| 7 | 2 | 0 | 4.91 | 14 | 2 | 1 | 12.4 | 18 | 3 | 1 | 22.1 |
| 7 | 3 | 0 | 5.49 | 14 | 3 | 0 | 12.5 | 18 | 4 | 0 | 22.2 |

TABLE 1-continued table of the various combinations of positive cavities in order to determine the initial concentration in the sample by the Most Probable Number (MPN) technique.

| Number of positive cavities | | | | Number of positive cavities | | | | Number of positive cavities | | | |
|---|---|---|---|---|---|---|---|---|---|---|---|
| 100 µl | 10 µl | 1 µl | MPN | 100 µl | 10 µl | 1 µl | MPN | 100 µl | 10 µl | 1 µl | MPN |
| 8 | 0 | 0 | 4.47 | 14 | 3 | 1 | 13.3 | 18 | 4 | 1 | 23.6 |
| 8 | 1 | 0 | 5.05 | 14 | 4 | 0 | 13.4 | 18 | 5 | 0 | 23.8 |
| 8 | 1 | 1 | 5.63 | 14 | 5 | 0 | 14.3 | 18 | 5 | 1 | 25.3 |
| 8 | 2 | 0 | 5.64 | 15 | 0 | 0 | 11.3 | 18 | 6 | 0 | 25.5 |
| 8 | 3 | 0 | 6.24 | 15 | 1 | 0 | 12.2 | 18 | 6 | 1 | 27.0 |
| 9 | 0 | 0 | 5.20 | 15 | 1 | 1 | 13.0 | 18 | 7 | 0 | 27.2 |
| 9 | 1 | 0 | 5.81 | 15 | 2 | 0 | 13.1 | 18 | 7 | 1 | 28.9 |
| 9 | 1 | 1 | 6.41 | 15 | 2 | 1 | 14.0 | 18 | 8 | 0 | 29.1 |
| 9 | 2 | 0 | 6.43 | 15 | 3 | 0 | 14.0 | 19 | 1 | 0 | 20.9 |
| 9 | 3 | 0 | 7.05 | 15 | 3 | 1 | 14.9 | 19 | 2 | 0 | 22.6 |
| 10 | 0 | 0 | 5.99 | 15 | 4 | 0 | 15.0 | 19 | 2 | 1 | 24.2 |
| 10 | 1 | 0 | 6.63 | 15 | 4 | 1 | 15.9 | 19 | 3 | 0 | 24.4 |
| 10 | 1 | 1 | 7.25 | 15 | 5 | 0 | 16.0 | 19 | 3 | 1 | 26.1 |
| 10 | 2 | 0 | 7.27 | 16 | 0 | 0 | 12.8 | 19 | 4 | 0 | 26.3 |
| 10 | 3 | 0 | 7.93 | 16 | 1 | 0 | 13.7 | 19 | 4 | 1 | 28.2 |
| 10 | 4 | 0 | 8.59 | 16 | 1 | 1 | 14.7 | 19 | 4 | 2 | 30.1 |
| 11 | 0 | 0 | 6.84 | 16 | 2 | 0 | 14.8 | 19 | 5 | 0 | 28.4 |
| 11 | 1 | 0 | 7.52 | 16 | 2 | 1 | 15.7 | 19 | 5 | 1 | 30.4 |
| 11 | 1 | 1 | 8.17 | 16 | 3 | 0 | 15.8 | 19 | 5 | 2 | 32.5 |
| 11 | 2 | 0 | 8.20 | 16 | 3 | 1 | 16.8 | 19 | 6 | 0 | 30.7 |
| 11 | 2 | 1 | 8.87 | 16 | 4 | 0 | 16.9 | 19 | 6 | 1 | 32.8 |
| 19 | 6 | 2 | 35.0 | 20 | 12 | 0 | 79.2 | 20 | 18 | 6 | 263 |
| 19 | 7 | 0 | 33.1 | 20 | 12 | 1 | 86.3 | 20 | 18 | 7 | 282 |
| 19 | 7 | 1 | 35.4 | 20 | 12 | 2 | 93.6 | 20 | 18 | 8 | 302 |
| 19 | 7 | 2 | 37.9 | 20 | 12 | 3 | 101 | 20 | 18 | 9 | 323 |
| 19 | 8 | 0 | 35.8 | 20 | 12 | 4 | 109 | 20 | 19 | 1 | 216 |
| 19 | 8 | 1 | 38.3 | 20 | 13 | 0 | 89.6 | 20 | 19 | 2 | 233 |
| 19 | 9 | 0 | 38.8 | 20 | 13 | 1 | 97.2 | 20 | 19 | 3 | 252 |
| 19 | 9 | 1 | 41.5 | 20 | 13 | 2 | 105 | 20 | 19 | 4 | 273 |
| 20 | 2 | 0 | 27.5 | 20 | 13 | 3 | 113 | 20 | 19 | 5 | 295 |
| 20 | 2 | 1 | 29.7 | 20 | 13 | 4 | 121 | 20 | 19 | 6 | 320 |
| 20 | 3 | 0 | 30.0 | 20 | 13 | 5 | 130 | 20 | 19 | 7 | 347 |
| 20 | 3 | 1 | 32.5 | 20 | 14 | 0 | 101 | 20 | 19 | 8 | 377 |
| 20 | 4 | 0 | 32.9 | 20 | 14 | 1 | 110 | 20 | 19 | 9 | 410 |
| 20 | 4 | 1 | 35.7 | 20 | 14 | 2 | 118 | 20 | 19 | 10 | 446 |
| 20 | 4 | 2 | 38.7 | 20 | 14 | 3 | 127 | 20 | 19 | 11 | 487 |
| 20 | 5 | 0 | 36.2 | 20 | 14 | 4 | 136 | 20 | 20 | 1 | 262 |
| 20 | 5 | 1 | 39.3 | 20 | 14 | 5 | 145 | 20 | 20 | 2 | 287 |
| 20 | 5 | 2 | 42.7 | 20 | 15 | 0 | 115 | 20 | 20 | 3 | 315 |
| 20 | 6 | 0 | 39.9 | 20 | 15 | 1 | 124 | 20 | 20 | 4 | 348 |
| 20 | 6 | 1 | 43.5 | 20 | 15 | 2 | 133 | 20 | 20 | 5 | 385 |
| 20 | 6 | 2 | 47.4 | 20 | 15 | 3 | 143 | 20 | 20 | 6 | 429 |
| 20 | 6 | 3 | 51.6 | 20 | 15 | 4 | 153 | 20 | 20 | 7 | 480 |
| 20 | 7 | 0 | 44.3 | 20 | 15 | 5 | 163 | 20 | 20 | 8 | 542 |
| 20 | 7 | 1 | 48.3 | 20 | 15 | 6 | 173 | 20 | 20 | 9 | 616 |
| 20 | 7 | 2 | 52.7 | 20 | 16 | 0 | 130 | 20 | 20 | 10 | 702 |
| 20 | 7 | 3 | 57.5 | 20 | 16 | 1 | 140 | 20 | 20 | 11 | 802 |
| 20 | 8 | 0 | 49.3 | 20 | 16 | 2 | 150 | 20 | 20 | 12 | 918 |
| 20 | 8 | 1 | 54.0 | 20 | 16 | 3 | 161 | 20 | 20 | 13 | 1050 |
| 20 | 8 | 2 | 59.0 | 20 | 16 | 4 | 172 | 20 | 20 | 14 | 1200 |
| 20 | 8 | 3 | 64.3 | 20 | 16 | 5 | 184 | 20 | 20 | 15 | 1390 |
| 20 | 9 | 0 | 55.3 | 20 | 16 | 6 | 196 | 20 | 20 | 16 | 1610 |
| 20 | 9 | 1 | 60.5 | 20 | 17 | 0 | 148 | 20 | 20 | 17 | 1900 |
| 20 | 9 | 2 | 66.1 | 20 | 17 | 1 | 160 | 20 | 20 | 18 | 2300 |
| 20 | 9 | 3 | 72.0 | 20 | 17 | 2 | 172 | 20 | 20 | 19 | 3000 |
| 20 | 10 | 0 | 62.2 | 20 | 17 | 3 | 184 | | | | |
| 20 | 10 | 1 | 68.1 | 20 | 17 | 4 | 197 | | | | |
| 20 | 10 | 2 | 74.2 | 20 | 17 | 5 | 210 | | | | |
| 20 | 10 | 3 | 80.7 | 20 | 17 | 6 | 224 | | | | |
| 20 | 10 | 4 | 87.3 | 20 | 17 | 7 | 239 | | | | |
| 20 | 11 | 0 | 70.2 | 20 | 18 | 1 | 184 | | | | |
| 20 | 11 | 1 | 76.6 | 20 | 18 | 2 | 198 | | | | |
| 20 | 11 | 2 | 83.4 | 20 | 18 | 3 | 213 | | | | |
| 20 | 11 | 3 | 90.3 | 20 | 18 | 4 | 228 | | | | |
| 20 | 11 | 4 | 97.4 | 20 | 18 | 5 | 245 | | | | |

It is quite possible for the distribution of the microorganisms, especially if they are not very numerous, not to be as uniform as in the examples below.

Referring to FIG. 3, it may be seen that there is microbial growth in all of the analysis cavities 9. On the other hand, in the small-sized analysis cavities 11 no growth has appeared. In the case of the medium-sized cavities 10, only eleven of the cavities out of twenty show any growth. If reference is then made to table 1, the 20/11/0 combination gives a Colony Forming Unit per gram of product (CFU/g) of 70 CFU/g. Knowing the initial dilution, which is 1/500, it is possible to deduce that the initial concentration of microorganisms was 70×500, i.e. 5000 CFU/g.

In FIG. 4, eighteen of the analysis cavities 9 show microbial growth. Likewise, three of the analysis cavities 10 and one of the analysis cavities 11 show growth. From this it may be deduced, in the same way as in the previous example, that the initial concentration was 22×500, i.e. 11000 CFU/g.

Figure 10:
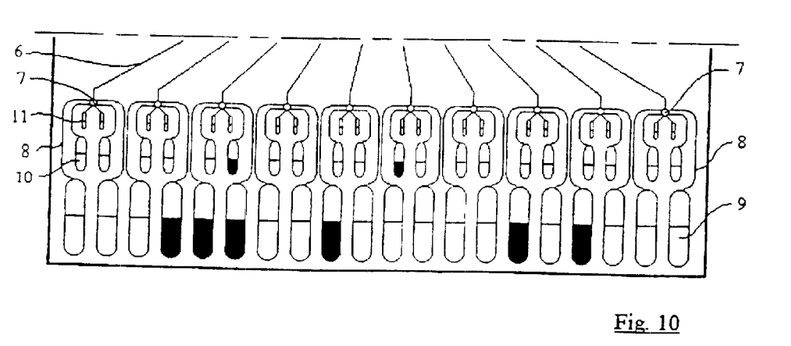
FIG. 10 shows an identical, but partial, view of FIG. 1, but in which the card has been used to count and characterize another sample containing microorganisms.

In FIG. 10, six of the twenty analysis cavities 9 show microbial growth. On the other hand, none of the cavities 11 is modified, whereas only two of the analysis cavities 10 show growth. It may therefore be deduced from this that, for this sample diluted 500 times, the initial concentration was 2100 CFU/g.

By reading the table, it will be understood that, for a sample diluted 500 times, it is possible to determine an initial microorganism concentration of between 225 and $1.5 \times 10^6$ CFU/g using a single analysis card 1 or 21, whereas the prior art generally uses four consumables in order to obtain such a range in the results. It is also possible to determine a concentration which would be less than or greater than these values without, however, knowing the precise concentration. It is then possible to make a further dilution tailored to the previous result so as to have a precise final result.

Of course, it is possible to have a different analysis card which comprises four or five, or even more, different sizes of cavities, in order to increase the field of investigation of the card.

Of course, it is possible to count other biological entities or materials, such as nucleic acids (DNA or RNA), antibodies or antigens. They may be revealed by anti-biological entity antibodies which are labeled.

It is possible to add to the tube 32 an immiscible liquid, of lower density than the sample 4, which will be sucked up after said sample 4 and which will serve to isolate the various quantities distributed in each cavity. It is also possible to have two tubes 32, one containing the biological sample and the other containing the isolating fluid, and to dip the pipe 33 alternately into the first tube 32 and then into the second tube 33. Finally, it is possible to have two pipes 33 on the card 1. Since the total volume of the cavities 9, 10 and 11 is 4440 µl and the volume of the sample 4 is 2220 µl, the volume of the isolating liquid may be 2220 µl. It may be less if it is desired for there to be air in the card 1 once it has been sealed, or greater if it is desired to be sure that the card has been completely filled with the sample 4 and the isolating liquid. In the latter case, this technique may be beneficial for growing anaerobic microorganisms.

In order for the volume of the sample 4 which has to be transferred into the card 1 to be determined precisely, there are three options which do not make use of automation.

The first option relates to filling the tube 32 with the precise amount of the sample 4. Since the flexible pipe 33 has its free end 34 at the lowest level of said sample 4, all of the sample 4 is transferred.

The second option relates to filling the card 1 with an amount of sample 4 which is predetermined by the position of the free end 34 immersed in said sample 4, within said tube 32. The sample 4 sucked up corresponds to the liquid column 4 lying above said end 34, and only this upper column of liquid is transferred.

Finally, the third option relates to filling the tube 32 with a very large amount of sample. By breaking the vacuum, the transfer is accomplished until the operator removes, directly or indirectly, the end 34 of the flexible pipe 33 from the sample 4, while still allowing the transfer of the fractions from said sample 4 into the cavities 9, 10 and 11 to continue.

It is therefore easy to understand that, when transferring the sample 4, the sampling takes place, firstly, level with said sample 4. It is therefore the level of the sample 4 which decreases until the free end 34 of the flexible pipe 33 is in the isolating fluid. Therefore, secondly, it is this fluid which is transferred into the card 1. Because of its density, which is lower than that of the sample 4, and because of the position of said card 1, as shown in FIG. 5, said fluid acts as a physical and biological barrier for the various small amounts of sample 4 delivered into the cavities 9, 10 and 11.

It is also quite possible to use a gelling agent in the medium. This technique can facilitate the isolation between the various cavities 9, 10 and 11 (FIG. 1) or 29, 30 and 31 (FIG. 2) with a gaseous fluid, such as air.

In order to check that the volume delivered into each cavity 9, 10 or 11 is approximately identical between cavities of the same size and between cavities of different sizes, tests were carried out.

Thus, with the small-sized cavities 11, three tests were carried out for the twenty wells. The tests were carried out using 2220 µl of demineralized water with a vacuum of 875 millibars. The results are given in table 2 and are the following:

TABLE 2 test of the distribution of the biological sample in small-sized cavities

|  | 1st test | 2nd test | 3rd test |
| --- | --- | --- | --- |
| 1st cavity | 0.95 | 1.01 | 1.01 |
| 2nd cavity | 0.95 | 1.02 | 1.06 |
| 3rd cavity | 0.98 | 1.02 | 1.04 |
| 4th cavity | 0.97 | 0.99 | 1.04 |
| 5th cavity | 0.98 | 1.04 | 1.00 |
| 6th cavity | 0.98 | 1.03 | 1.03 |
| 7th cavity | 0.99 | 1.03 | 0.99 |
| 8th cavity | 0.99 | 1.04 | 0.99 |
| 9th cavity | 0.94 | 1.02 | 1.00 |
| 10th cavity | 0.94 | 1.05 | 1.02 |
| 11th cavity | 0.98 | 1.02 | 0.99 |
| 12th cavity | 0.91 | 1.05 | 1.02 |
| 13th cavity | 1.01 | 1.01 | 0.96 |
| 14th cavity | 1.00 | 1.02 | 1.04 |
| 15th cavity | 0.96 | 1.02 | 1.01 |
| 16th cavity | 1.02 | 1.03 | 0.99 |
| 17th cavity | 1.02 | 1.03 | 0.99 |
| 18th cavity | 1.02 | 1.00 | 1.02 |
| 19th cavity | 1.01 | 0.99 | 1.01 |
| 20th cavity | 1.01 | 1.01 | 1.02 |
| Average | 0.98 | 1.02 | 1.01 |
| Standard deviation | 0.032 | 0.018 | 0.025 |
| Coefficient of variation | 3.3% | 1.7% | 2.4% |

Likewise with the medium-sized cavities 10, three tests were carried out for the twenty wells. The tests were carried out using 2220 µl of demineralized water with a vacuum of 875 millibars. The results are given in table 3 and are the following:

TABLE 3 test of the distribution of the biological sample in medium-sized cavities.

|  | 1st test | 2nd test | 3rd test |
|---|---|---|---|
| 1st cavity | 8.8 | 9.1 | 10.1 |
| 2nd cavity | 12.5 | 10.5 | 10.1 |
| 3rd cavity | 9.6 | 9.4 | 10.5 |
| 4th cavity | 10.6 | 10.9 | 9.3 |
| 5th cavity | 10.8 | 9.1 | 8.6 |
| 6th cavity | 10.5 | 10.3 | 10.6 |
| 7th cavity | 10.0 | 9.6 | 9.4 |
| 8th cavity | 10.7 | 11.3 | 10.8 |
| 9th cavity | 9.3 | 10.0 | 10.7 |
| 10th cavity | 10.2 | 10.3 | 9.9 |
| 11th cavity | 9.9 | 9.4 | 10.3 |
| 12th cavity | 9.1 | 10.3 | 11.5 |
| 13th cavity | 9.3 | 9.1 | 10.1 |
| 14th cavity | 9.7 | 8.7 | 9.2 |
| 15th cavity | 11.5 | 11.6 | 11.3 |
| 16th cavity | 10.7 | 9.7 | 7.7 |
| 17th cavity | 9.5 | 10.3 | 10.5 |
| 18th cavity | 9.9 | 9.2 | 11.0 |
| 19th cavity | 11.1 | 9.4 | 11.8 |
| 20th cavity | 9.7 | 8.4 | 10.2 |
| Average | 10.2 | 9.8 | 10.2 |
| Standard deviation | 0.897 | 0.834 | 0.985 |
| Coefficient of variation | 8.8% | 8.5% | 9.7% |

In an identical manner to the previous two cases, three tests using the large-sized cavities 9 were carried out for the twenty wells. The tests were carried out under the same conditions as previously, that is to say using 2220 µl of demineralized water with a vacuum of 875 millibars. The results are given in table 4 which follows:

TABLE 4 test of the distribution of the biological sample in large-sized cavities.

|  | 1st test | 2nd test | 3rd test |
|---|---|---|---|
| 1st cavity | 93.2 | 98.7 | 97.8 |
| 2nd cavity | 101.5 | 101.1 | 100.2 |
| 3rd cavity | 97.9 | 99.6 | 95.3 |
| 4th cavity | 100.4 | 103.2 | 99.8 |
| 5th cavity | 98.5 | 98.4 | 98.9 |
| 6th cavity | 101.7 | 100.8 | 99.7 |
| 7th cavity | 103.8 | 101.9 | 101.4 |
| 8th cavity | 100.3 | 97.0 | 101.9 |
| 9th cavity | 102.4 | 102.8 | 99.9 |
| 10th cavity | 99.1 | 99.8 | 99.9 |
| 11th cavity | 105.5 | 101.4 | 99.8 |
| 12th cavity | 100.7 | 103.1 | 99.2 |
| 13th cavity | 100.9 | 99.8 | 100.3 |
| 14th cavity | 104.2 | 101.0 | 102.4 |
| 15th cavity | 95.7 | 98.5 | 102.5 |
| 16th cavity | 102.6 | 98.1 | 98.5 |
| 17th cavity | 103.2 | 99.3 | 98.4 |
| 18th cavity | 102.6 | 101.7 | 98.5 |
| 19th cavity | 102.2 | 95.4 | 95.9 |
| 20th cavity | 101.1 | 97.6 | 104.3 |
| Average | 100.9 | 100.0 | 99.7 |
| Standard deviation | 2.904 | 2.123 | 2.133 |
| Coefficient of variation | 2.9% | 2.1% | 2.1% |

It should be noted, on the one hand, that the volume present in each well or cavity 9, 10 or 11 of the same size is relatively constant since the average of the three tests is approximately constant, and that the standard deviation and the coefficient of variation are small.

In fact, the standard deviation is constant whatever the volume for this reason there is a decrease in the coefficient of variation, which is proportional to the increase in the volume of liquid contained in the sample. In fact, these results are due to the problems of the accuracy in the measurements of liquids present in each well or cavity 9, 10 or 11 after delivering the initial sample.

Nevertheless, these results are particularly beneficial and allow the use of the method for calculating the concentration of any biological material, such as nucleic acids, antibodies or microorganisms, present in said initial biological sample 4.

The analysis card 1 can also be used in the medical field for counting microorganisms in biological liquids.

The following example describes the protocol that can be employed within the context of analyzing urine in order to count urinary microbes. The urine taken is diluted by transferring (after homogenization) from the sampling container a 10 µl calibrated dose into a tube containing 5 ml of a culture medium.

After homogenization, a $2 \times 10^{31}$ $^3$, i.e. 1/500 dilution is obtained. Next, 2220 µl of this dilution are transferred [lacuna] the tube 32. Next, the card 1 is filled, then incubated and finally read in the same way as in the examples described above. However, the incubation temperature will be higher and close to 37° C.

Using this protocol, it is therefore possible to count the urinary microbes when the contamination of the urine is between 225 CFU/ml and $1.5 \times 10^6$ CFU/ml.

REFERENCES

1. Analysis card
2. Body of the analysis card 1
3. Injection region in the card 1
4. Biological liquid or sample to be analyzed
5. Main feed channel
6. Secondary channels
7. Wells corresponding to each channel 6 or delivery means
8. Terminal channels
9. Large-sized terminal analysis cavities corresponding to a channel 8
10. Medium-sized terminal analysis cavities corresponding to a channel 8
11. Small-sized terminal analysis cavities corresponding to a channel 8
12. Main delivery well or means
13. Lateral injection region
14. Circular groove in the body 2
15. Shoulder of the pipe 33 fitting into the groove 14
21. Analysis card
22. Body of the analysis card 21
23. Injection region in the card 21
25. Feed channels
27. Wells corresponding to each channel 25 or delivery means
28. Terminal channels
29. Large-sized terminal analysis cavities corresponding to a channel 28
30. Medium-sized terminal analysis cavities corresponding to a channel 28
31. Small-sized terminal analysis cavities corresponding to a channel 28
32. Tube containing the sample 4
33. Pipe linking the region 3 to the tube 32
34. Free end of the pipe 33
35. Transparent adhesive film
101. Analysis card
102. Body of the analysis card 101
103. Injection region in the card 101

104. Overflow
105. Main feed channel
106. Secondary channels for the cavities 109
107. Secondary channels for the cavities 110
108. Secondary channels for the cavities 111
109. Large-sized terminal analysis cavities corresponding to a channel 106
110. Medium-sized terminal analysis cavities corresponding to a channel 107
111. Small-sized terminal analysis cavities corresponding to a channel 108.
112. Wells for retarding the flow of the sample 4 in the main channel 105 at the cavities 109 or 110
113. Upper branch-off for the cavities 109 or 110
114. Well for preventing flow of the sample 4 into the branch-offs 113
115. Branch-off for bypassing the cavities 109, 110 or 111
116. Well for retarding the flow of the sample 4 into the main channel 105 at the cavities 111
117. Lower branch-off for the cavities 111
118. Well for preventing flow of the sample 4 into the branch-off 117
119. Means for draining the sample 4
120. Bottom of the body 102 of the card 101 at a cavity 109, 110 or 111
121. Valve between the injection region 103 and the main channel 105.
122. Valve between the two levels of the cavities 109
123. Valve between the cavities 109 and the cavities 110
124. Valve between the two levels of the cavities 110
125. Valve between the cavities 110 and the cavities 111
126. Valve between the two levels of the cavities 111
127. Outlet of the overflow 104
F1. Inflow of the sample 4 via the main channel 5 into a secondary channel 106, 107 or 108
F2. Inflow of the sample 4 via a secondary channel 106, 107 or 108 into a cavity 109, 110 or 111
F3. Transfer of air via the upper branch-off 113 of the cavities 109 or 110
F4. Transfer of the sample 4 via the main channel 5 at the cavities 109, 110 or 111
F5. Outflow of the sample 4 via the main channel 5 at the cavities 109, 110 or 111
F6. Transfer of air and/or of sample 4 via the lower branch-off 117 of the cavities 111

What is claimed is:

1. Analysis card (1) which comprises a body (2) consisting of:
    a region (3) for injecting a biological liquid (4) to be analyzed into the card (1),
    a main feed channel (5) for the biological liquid (4) coming from the injection region (3),
    at least two secondary channels (6) lying in the extension of the main channel (5), and
    at least one well (7) corresponding to each secondary channel (6),
characterized in that each well (7) constitutes a means of delivering a predetermined volume of said biological liquid (4) into at least two terminal analysis cavities (9, 10 or 11), via a terminal channel (8) for each analysis cavity (9, 10 or 11), and in that the total volume (4) to be analyzed is less than the total volume of all of the analysis cavities (9, 10 and 11).

2. Analysis card (21) which comprises a body (22) consisting of:
    a region (23) for injecting a biological liquid to be analyzed into the card (21),
    at least two feed channels (25) for the biological liquid coming from the injection region (23), and
    at least one well (27) corresponding to each feed channel (25),
characterized in that each well (27) constitutes a means of delivering a predetermined volume of said biological liquid into at least two terminal analysis cavities (29, 30 or 31), via a terminal channel (28) for each analysis cavity (29, 30 or 31), and in that the volume to be analyzed is less than the total volume of all of the analysis cavities (29, 30 and 31).

3. Card according to either of claim 1 or 2, characterized in that the delivery of the biological liquid (4) into the terminal analysis cavities (9, 10 and 11 or 29, 30 or 31) takes place in parallel.

4. Analysis card (101) which comprises a body (102) consisting of:
    a region (103) for injecting a biological liquid (4) to be analyzed into the card (101),
    a main feed channel (105) for the biological liquid (4) coming from the injection region (103),
    at least two secondary channels (106, 107 and/or 108) lying in the extension of the main channel (105), and
    at least one cavity (109, 110 and/or 111) corresponding to each secondary channel (106, 107 or 108),
characterized in that each cavity (109, 110 or 111) constitutes a means of receiving a predetermined volume of said biological liquid (4) and in that the volume to be analyzed, introduced into the card, is greater than the total volume of all of the analysis cavities (109, 110 and 111).

5. Card according to claim 4, characterized in that the delivery of the biological liquid (4) into the analysis cavities (109, 110 or 111) takes place in series and is followed by a purge.

6. Card according to claim 1, characterized in that a well (12), acting as a main means of delivering the biological liquid (4), is present between, on the one hand, the main channel (5) and, on the other hand, the secondary channels (6).

7. Card according to any one of claim 1, 2 or 6, characterized in that the volumes of the secondary channels (6) or of the feed channels (25) are all identical.

8. Card according to any one of claims 1 to 7, characterized in that the terminal analysis cavities (9, 10 and/or 11 or else 29, 30 and/or 31 or else 109, 110 and/or 111) are of at least two different volumes.

9. Card according to any one of claims 1 to 8, characterized in that the terminal analysis cavities (9, 10 and/or 11 or else 29, 30 and/or 31 or else 109, 110 and/or 111) are of three different volumes.

10. Card according to either of claim 8 or 9, characterized in that the ratio existing between two cavities of different volumes (9 and 10 or 10 and 11 or 9 and 11 or else 29 and 30 or 30 and 31 or 29 and 31 or else 109 and 110 or 110 and 111 or 109 and 111) is between 1/5 and 1/20, 1/50 and 1/200 or 1/500 and 1/2000, and especially 1/10, 1/100 or 1/1000.

11. Card according to any one of claims 1 to 9, characterized in that the cavities (9, 10 and/or 11 or else 29, 30 and/or 31 or else 109, 110 and/or 111) of the same volume are arranged geometrically (aligned or concentric) in order to facilitate the read-out.

12. Method of filling an analysis card (1 or 21), as presented according to any one of claims 1 to 3, 6 or 7, characterized in that it consists in:
    connecting the injection region (3 or 23) of the card (1 or 21) to a volume of a the [sic] biological sample (4) to be analyzed, creating a vacuum within and/or in the vicinity of said card (1 or 21), breaking the vacuum so as, on the one hand, to transfer the biological liquid (4) into the analysis cavities (9, 10 and/or 11 or else 29, 30 and/or 31) and, on the other hand, to isolate with an inert fluid the various fractions of the sample which come from said biological liquid (4) and which are present in each of said analysis cavities (9, 10 or 11 or else 29, 30 or 31) and analyzing the result obtained so as to determine the amount of microorganisms or of any other biological component, such as nucleic acids, antibodies, present in the initial biological sample (4).

13. Method of filling an analysis card (101) as presented according to either of claim 4 or 5, characterized in that it consists in:

connecting the injection region (103) or the outlet (127) of the card (101) to a volume of a the [sic] biological sample (4) to be analyzed, creating a vacuum or an overpressure within and/or in the vicinity of said card (101) so as to transfer the biological liquid (4) into the analysis cavities (109, 110 and/or 111), stopping the vacuum or the overpressure, purging the main channel (105) in order to isolate with an inert fluid the various fractions of the sample which come from said biological liquid (4) and which are present in each of said analysis cavities (109, 110 or 111), and analyzing the result obtained so as to determine the amount of microorganisms or of any other biological component, such as nucleic acids, antibodies, present in the initial biological sample (4).

14. Method according to claim 12, characterized in that, once the vacuum has been broken, the isolating fluid is in contact with the biological liquid (4) either in the secondary channels (6) or feed channels (25) or in the analysis cavities (9, 10 and/or 11 or else 29, 30 and/or 31).

15. Method according to either of claim 12 or 14, characterized in that the volume of the biological liquid (4) to be analyzed is less than the total volume of all of the analysis cavities (9, 10 and 11 or else 29, 30 and 31).

16. Method according to claim 13, characterized in that the volume of the biological liquid (4) to be analyzed is greater than or equal to the total volume of all of the analysis cavities (109, 110 and 111), of all of the fluid circuit (105 to 108 and 112 to 118) and of the overflow (104).

17. Method according to either of claim 13 or 16, characterized in that the volume of the biological liquid (4) to be analyzed is greater than or equal to the total volume of all of the analysis cavities (109, 110 and 111) and of all of the fluid circuit (105 to 108 and 112 to 118).

18. Method according to any one of claim 12, 14 or 15, characterized in that the ratio of the volume of the biological liquid (4) to be analyzed to the total volume of all of the analysis cavities (9, 10 and 11 or else 29, 30 and 31) is from 1/10 to 9/10, especially from 4/10 to 6/10, and preferably 5/10.

19. An analysis card (1, 21 or 101), according to any one of claims 1 to 11, for counting microorganisms using the technique of the most probable number.

* * * * *